(12) United States Patent
Nikawa et al.

(10) Patent No.: US 8,026,207 B2
(45) Date of Patent: Sep. 27, 2011

(54) PEPTIDES AND COMPOSITIONS FOR INHIBITING FUNGAL GROWTH

(75) Inventors: Hiroki Nikawa, Hiroshima (JP); Masahiro Nishimura, Hiroshima (JP); Koichiro Tsuiji, Hiroshima (JP); Ryoko Kawabata, Hiroshima (JP); Nobue Hiromoto, Hiroshima (JP)

(73) Assignees: Japan Science and Technology Agency, Kawaguchi-shi (JP); Hiroshima University, Higashi-Hiroshima-shi (JP); Two Cells Co., Ltd., Hiroshima-shi (JP)

( * ) Notice: Subject to any disclaimer, the term of this patent is extended or adjusted under 35 U.S.C. 154(b) by 387 days.

(21) Appl. No.: 11/992,552

(22) PCT Filed: Sep. 6, 2006

(86) PCT No.: PCT/JP2006/317621
§ 371 (c)(1),
(2), (4) Date: Dec. 9, 2008

(87) PCT Pub. No.: WO2007/034678
PCT Pub. Date: Mar. 29, 2007

(65) Prior Publication Data
US 2009/0253636 A1    Oct. 8, 2009

(30) Foreign Application Priority Data
Sep. 26, 2005   (JP) ................................ 2005-277121

(51) Int. Cl.
*A61K 38/04*   (2006.01)
*C07K 9/00*    (2006.01)
*C07K 9/14*    (2006.01)
*C07K 9/20*    (2006.01)

(52) U.S. Cl. ............ 514/1.1; 514/3.3; 514/3.4; 530/327

(58) Field of Classification Search .................... None
See application file for complete search history.

(56) References Cited

FOREIGN PATENT DOCUMENTS

| JP | 2002-179698 | 6/2002 |
|---|---|---|
| JP | 179699 | 6/2002 |
| JP | 3472821 B2 | 9/2003 |
| JP | 3546231 B2 | 4/2004 |

OTHER PUBLICATIONS

Futakawa, Hiroki et al. "Shinki Gosei Peptide no Satsu-Candida Sayo ni Kansuru Kenkyu" Fungicidal Activity of Synthetic Peptides, Japan Prosthodontic Society Gakujutsu Taikai Shorokushu (2002), vol. 107, pp. 74.
Nikawa et al., Oral Diseases, vol. 10, pp. 221-228 (2004).

*Primary Examiner* — Prema Mertz
(74) *Attorney, Agent, or Firm* — Birch, Stewart, Kolasch & Birch, LLP.

(57) ABSTRACT

It is intended to provide a novel peptide which can exert higher antifungal effect also on a patient whose organ function is impaired with no side effect problems. The peptide comprises the following amino acid sequence: (1) SEQ ID NO:1: Lys -Arg-Leu-Phe-Arg-Arg-Trp-Gln-Trp-Arg-Tyr, (2) SEQ ID NO:2: Arg-Arg-Trp-Gln -Trp-Arg-Met-Lys-Lys-Tyr, (3) SEQ ID NO:3: Lys-Arg-Trp-Gln-TTp-Arg-Leu-Tyr, or (4) SEQ ID NO:4: Lys-Arg-Leu-Phe-Lys-Tyr, an antifungal agent comprising the peptide, a composition having a fungicidal and/or growth inhibitory action against fungus containing an effective amount of the peptide as an active ingredient, a medical apparatus/device which contains the peptide, whereby a fungicidal action is conferred, and a fungicidal and/or growth inhibiting method against fungus comprising administering the peptide and the like.

9 Claims, 4 Drawing Sheets

PEPTIDES AND COMPOSITIONS FOR INHIBITING FUNGAL GROWTH

TECHNICAL FIELD

The present invention relates to a novel peptide, especially to a novel peptide having a fungicidal and/or growth inhibitory action and a composition comprising said peptide.

BACKGROUND OF THE INVENTION

Most of fungi having pathogenicity for human have two-phase property that is to say, they can take both a yeast form and a mycelium form depending on environmental conditions. Some of the fungi do not have the two-phase property. In the yeast form, they exist as a single cell having a egg-like sphere, and will divide and grow through a process of budding. The mycelium form show a branched filamentous structure that is called mycelium, which consists of tandem cells with a cylindrical-shape or of multinuclear and elongated cells.

Such fungi include *Candida, Cryptococcus, Aspergillus*, etc. *Candida* are a normal inhabitant in oropharynges and digestive organs of healthy individuals. *Cryptococcus* are not only very often contained in soul and feces of a pigeon and a mouse, but also present in a humid place such as in a room. They will be carried by wind and contact humans. *Aspergillus* have been found since early times in soul and feces of birds, and recently they are very often found also in an air conduct and filter in a hospital. Although these fungi have a low infectious capacity for healthy individuals, they will release tissue-destructing substances such as exotoxin, endotoxin and protease. Most of the fungi will grow in patients receiving administration of anticancer agents, immunosuppressive agents, steroid agents, and broad-spectrum antibiotics, and show characteristics of opportunistic infection. Cell-mediated immunity in healthy individuals would sufficiently function against these fungi and serve as phylaxis. But, as the cell-mediated immunity in the above patients has been compromised, the infection would be permitted. Especially, in the cases of patients suffering from malignant diseases, patients with a transplanted organ, patients treated in an intensive care unit and the like, the above fungi would cause deep-seated mycosis such as deep candidiasis, or candidaemia, and would often have a severe outcome.

Amphotericin B belonging to polyenes is known as a therapeutic agent against these mycotic diseases. Antifungal agents such as flucytosine, ketoconazole and miconazole of imidazoles are known as well.

[Patent Document 1] Japanese Patent No. 3472821, Novel peptide, and Composition comprising the peptide
[Patent Document 2] Japanese Patent No. 3546231, Novel peptide, and Composition comprising the peptide
[Non-Patent Document 1] Oral Diseases (2004) 10, 221-228, Fungicidal effect of three new synthetic cationic peptides against *Candida albicans*

DISCLOSURE OF THE INVENTION

Problems to be Solved by the Present Invention

However, the above prior antifungal agents have a problem of strong side effects such as a dose-dependent renal toxic effect. Especially, as some of the antifungal agents acting on ergosterol of the fungi such as *Candida* are similar to sterols such as cholesterol in a living cell membrane, they will cause side effects. Furthermore, the conventional antifungal agents exercise an influence so widely on normal cells of a patient with organ malfunction that it will be difficult to use them for such patient. It has been reported that the effects by the antifungal agents were very limited especially against non-albicans *Candida*. Furtheremore, the emergence of anti-drug strains against polyenes has been reported since late 1970s, and recently it has been revealed that an anti-drug strain with an anti-drug system against azole antifungal agents is present. Accordingly, it would be desired to use an antifungal agent that can exert a higher antifungal effect on a patient whose organ function is impaired without causing any side effect problems. However, there is no such antifungal agent at the moment.

The present inventors had studied anti fungal peptides comprised in living bodies or milk to solve the above problems, and already found a novel peptide showing a potential antifungal function:
Lys-Arg-Leu-Phe-Arg-Arg-Trp-Gln-Trp-Arg-Met-Lys-Lys-Tyr (SEQ ID NO: 5)(referred to as "JH8194" hereinafter), and had obtained Japanese Patent No.3472821.

The main purpose of the present invention is therefore to provide an antifungal agent that can exert the higher antifungal effect with no side effect problems on a patient whose organ function is impaired.

Means to Solve the Problems

The present inventors have accomplished the present invention on the basis of the finding that deletion of three amino acid residues that are underlined in the following amino acid sequence of JH-18194 will significantly increase its antifungal activity beyond expectation:
Lys-Arg-Leu-Phe-Arg-Arg-Trp-Gln-Trp-Arg-Met-Lys-Lys-Tyr (SEQ ID NO: 5)

Various kinds of its variants have been also prepared on the basis of the amino acid sequence of JH8194.

Thus, the present invention relates to the following aspects:
[1] A peptide consisting of one of the following amino acid sequences:

(1) SEQ ID NO: 1: Lys-Arg-Leu-Phe-Arg-Arg-Trp-Gln-Trp-Arg-Tyr ([JH8194Y]);

(2) SEQ ID NO: 2: Arg-Arg-Trp-Gln-Trp-Arg-Met-Lys-Lys-Tyr ([8194F]);

(3) SEQ ID NO: 3: Lys-Arg-Trp-Gln-Trp-Arg-Leu-Tyr ([8194W]);

or (4) SEQ ID NO: 4: Lys-Arg-Leu-Phe-Lys-Tyr ([8194-6]).

[2] An antifungal agent comprising the peptide according to Claim 1.
[3] The antifungal agent according to Claim 2 wherein the fungus is *Candida, Cryptococcus*, or *Aspergillus*.
[4] A composition having a fungicidal and/or growth inhibitory function against fungus, comprising an effective amount of the peptide according to Claim 1 as an active ingredient.
[5] A pharmaceutical composition consisting of the composition according to Claim 4.
[6] A cleaning agent, fungicide or collutorium consisting of the composition according to Claim 4.
[7] A pharmaceutical composition according to any one of Claims 4-6 wherein the fungus is *Candida, Cryptococcus*, or *Aspergillus*.

[8] A medical device or apparatus containing the peptide according to Claim 1 and being provided with antifungal property.
[9] A fungicidal and/or growth inhibiting method against fungus, comprising administering the peptide according to Claim 1.
[10] A fungicidal and/or growth inhibiting method against fungus, comprising administering the antifungal agent according to Claim 2.
[11] A fungicidal and/or growth inhibiting method against fungus, comprising administering the composition according to Claim 4.
[12] The method according to any one of Claims 9-11, wherein the fungus is *Candida, Cryptococcus*, or *Aspergillus*.

ADVANTAGES OF THE INVENTION

The peptide according to the present invention has an advantage in synthesis with respect to its cost and the like as it is a molecule with a low molecular weight consisting of 6-11 amino acids. Furthermore, it shows significant antifungal and fungicidal effects against fungi at a much lower concentration than that of the conventional antifungal peptides or antifungal agents. Its application as an antifungal agent for medical or research purposes would therefore be of great advantage.

BEST MODE FOR CARRYING OUT THE PRESENT INVENTION

Figure 1:
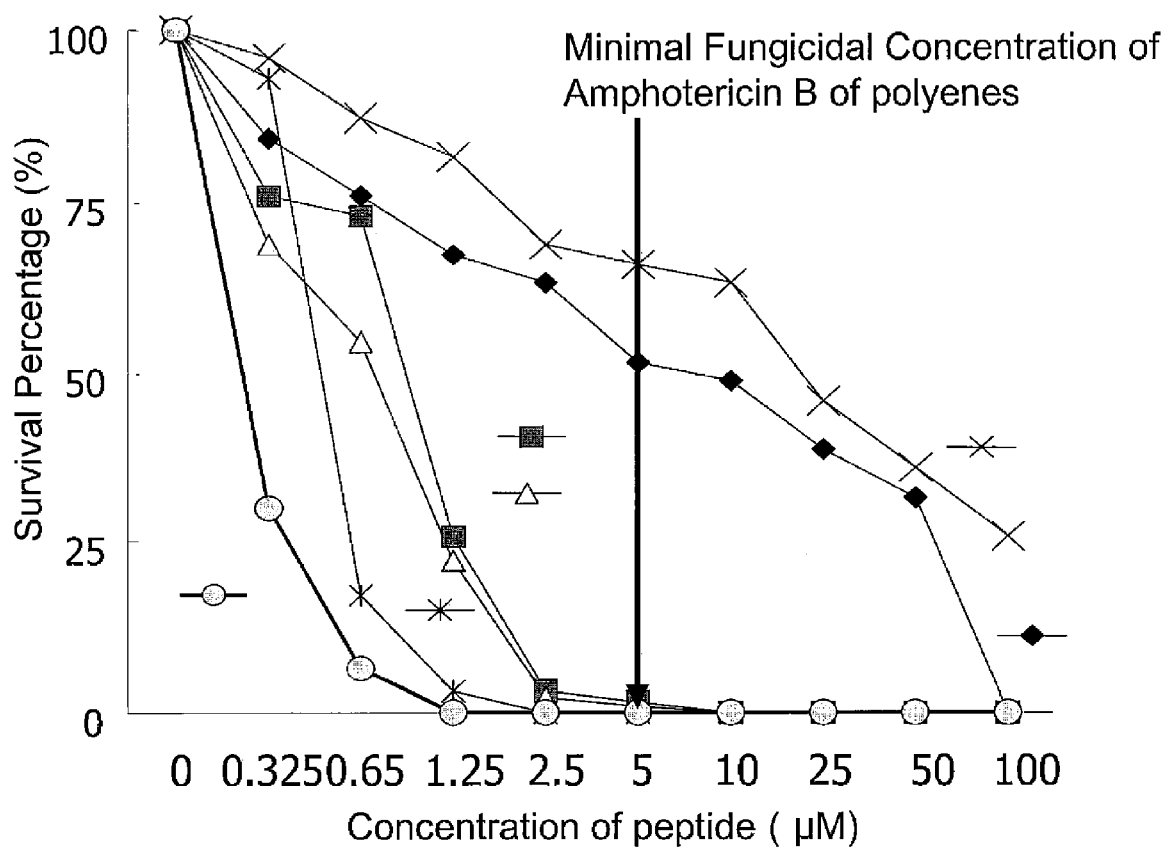
FIG. 1 is a graph showing the antifungal effects of the present peptides and prior peptide.

The peptide according to the present invention consists of 6-11 amino aicds, and may be produced by a conventional method such as a peptide synthesis method. The terms "Lys", "Arg", "Leu", "Phe", "Ser", "Tyr" and "Met" stand for Lysine, Arginine, Leucine, Phenylalanine, Serine, Tyrosine, and Methionine, respectively. As shown by the following examples, the novel peptides according to the present invention have significant fungicidal and/or growth inhibitory action against fungi. The peptide according to the present invention is therefore useful as an antifungal agent.

The peptide according to the present invention may be obtained by any peptide synthesis method well known in the art. The present peptide may be prepared both in a liquid-phase method and solid-phase method. In the liquid-phase method, a reaction is generally carried out in a solution state, and a product is isolated and purified from the reaction mixture to be used as an intermediate for the next peptide elongation reaction. In the solid-phase method, an amino acid is fixed onto a solid carrier that is insoluble in a reaction solvent, and condensation reactions are sequentially carried out with the thus fixed amino acid so as to elongate a peptide chain.

In a basic chemical synthesis of a peptide, an amino acid with a protected carboxyl group is condensed with an amino acid with a protected amino group to form a peptide bond. After an amino-protecting group is removed, the resulting free amino group is then condensed with another amino acid with a protected amino group. Such reactions are sequentially repeated so as to elongate the peptide by one amino acid from its C-end to N-end. In the condensation reaction, the carboxyl group is activated and reacted with the amino group. The activation method may be selected from dicyclocarbodiimide (DCC) method, activated ester method, acid anhydride method, azide method and the like, depending on the degree of reactivity and side effects such sa racemization. A protecting group will be introduced into the amino group, carboxyl group and a functional side group (R) in order to inhibit their side reaction during the condensation. Preferably, such protecting group is stable under the conditions of the condensation reaction, but may be rapidly removed when necessary. The protecting group of the amino group or the carboxyl group is preferably removed alternatively.

The amino protecting group includes benzyloxycarbonyl (Bz), t-butylbutoxycarbonyl (Boc), p-bipehnylisopropyloxycarbonyl, 9-fluorenylmethyloxycarbonyl (Fmoc) and the like. The carboxyl protecting group includes a group being able to constitute alkylester and benzylester groups. In the solid-phase method, however, the carboxyl group at its C-end is bound to the carrier made of chlorotrityl resin, chloromethyl resin, oxymethyl resin, p-alkoxylbenzylalcohol resin and the like. The condensation reaction is carried out in the presence of a condensing agent such as carbodiimide, or using an N-protected amino acid-activating ester or a peptide-activating ester.

After the completion of the condensation reaction, the protecting group shall be removed, and the bond between C-end of the resulting peptide and resin will be cleaved in the case of the solid-phase synthesis. The peptide according to the present invention may be further purified in accordance with a conventional method such as ion-exchange chromatography, reversed-phase liquid chromatography, affinity chromatography and the like. An amino acid sequence of the thus synthesized peptide may be confirmed by a protein sequencer determining an amino acid sequence from its C-end by means of Edman degradation method, GC-MS and the like.

The "fungus" in the present specification includes any one that belongs to any genus known for those skilled in the art such as *Candida, Cryptococcus, Aspergillus* or *Trichophyton*.

The composition according to the present invention comprises an effective amount of the present peptide, and has significant fungicidal and/or growth inhibitory action against fungi. The present composition may be applied in many ways as described below. Thus, the present invention relates to a fungicidal and/or growth inhibiting method against fungus, comprising administering the peptide, antifungal agent comprising said peptide or said composition.

For example, where the composition according to the present invention is a pharmaceutical one, the peptide of the present invention may be comprised in an amount sufficient enough to effect the fungicidal and/or growth inhibitory action against fungi. It may be contained at a ratio of, for example, 0.001-0.01 wt %, preferably 0.005-0.01 wt %. Below 0.001 wt %, the effects of the present peptide cold not be obtained, and over 0.02 wt %, hemolyisis would not occur.

The present pharmaceutical composition may be orally, parenterally and intrarectally administered, oral administration being preferable. A dose of the peptide comprised in the composition may differ depending on the administration route, the conditions and age of patients, and the like, being usually 1-10 mg/kg per dose, preferably 5-10 mg/kg per dose, and it may be administered once to several times (about 5-7 times) per day.

The present pharmaceutical composition may comprise any substances known as pharmaceutically acceptable carriers or auxiliaries for those skilled in the art in addition to the present peptide as the active ingredient. It is required that such substances would not substantially react wit the peptide according to the present invention.

As examples of the above pharmaceutically acceptable carriers or auxiliaries, there may be mentioned lactose, glucose, mannitol, dextrin, cyclodextrin, starch, sucrose, magnesium meta-silicate aluminate, synthesized aluminum silicate, sodium carboxylmethyl cellulose, hydroxypropyl starch, calcium carboxylmethyl cellulose, ion-exchange resin, methyl cellulose, gelatin, gum arabic, hydroxypropyl cellulose, hydroxymethyl cellulose, polyvinyl pyrrolidone, polyvinyl alcohol, soft anhydrous silicate, magnesium stearate, talc, tragacanth, bentonite, bee gum, titan oxide, sorbitan fatty acid ester, sodium laurylsulfate, glycerin, fatty acid glycerin ester, purified lanoline, glycerogelatin, polysorbate, macrogol, vegetable oil, wax, fluid paraffin, white petrolatum, fluorocarbon, nonionic surfactant, propylenglycol, water, etc.

The pharmaceutical composition of the present invention may be formulated into any form depending on the administration route, the conditions and age of patients and the like, such as pill, capsule, granule, powder, syrup, suspension, suppository, ointment, cream, gel agent, adhesive skin patch, injectable solution, etc. These formulation may be prepared according to conventional methods. A liquid formulation may be solved or suspended in a suitable solvent such as water when applied. The pill and granule may be coated by any know method. The injectable solution may be prepared by solving the peptide of the present invention in water, or in physiological saline or glucose solution, if necessary which may be optionally mixed with a buffer or preservative.

The present composition have a variety of use such as a cleaning agent, fungicide or collutorium.

In the case of using the composition of the present invention as the cleaning agent, fungicide or collutorium, an optimum content of the peptide of the present invention in the composition may be optionally selected depending on a kind of the medical devices or apparatuses to be cleaned, an extent of contamination by the fungi and the like. For example, the present peptide may be in a range of 0.1 μM-several tens μM in the cleaning agent or collutorium. Even with such a low concentration of the peptide, a sufficient antifungal effects can be shown. The peptide according to the present invention will be used at a rage preferably of 0.3 μM-5 μM, more preferably of 0.6 μM-2.5 μM, not being constrained in these ranges, though.

Like the pharmaceutical composition of the present invention, the above compositions may also comprise any substances known as suitable carriers or auxiliaries for those skilled in the art in addition to the present peptide as the active ingerdient.

Furthermore, the antifungal agent comprising the peptide according to the present invention may be contained in raw material or stuff of various medical devices or apparatuses such as contact lenses in order to produce various medical devices or apparatuses that are provided with antifungal property. Such medical devices or apparatuses may be easily produced by any process known for those skilled in the art, for example, by mixing the raw material or stuff with the peptide of the present invention by an appropriate method, or by forming the raw material or stuff and coating their surface with the peptide of the present invention by a suitable method such as applying or spraying.

The present invention will be specifically explained below with reference to the examples, which should not be construed to limit the scope of the present invention. The contents of the prior arts referred to in this specification are considered to be incorporated as a whole as a part of the disclosure of the present specification.

EXAMPLE

Antifungal Test 1

The antifungal action against *Candida* was examined in order to confirm the antifungal effect of the present peptide. The peptide was synthesized by a conventional amino acid synthesis method using a peptide synthesizer manufactured by Shimazu Co. of Japan. The strain of Candida was isolated and provided from oral cavity of a patient in Glasgowden Hospital. The antifungal effect of the present peptide was evaluated using the above Candida strain according to the method of Edgerton et al (1998). Twenty μl of the suspension of *C. albicans* ($1.8 \times 10^5$ cfu/mL) was mixed with the same amount of a peptide solution (0.325 μM-25 μM of the peptide concentration) and incubated for 90 min at 37° C. The reaction was stopped by adding Yeast Nitrogen Base medium. The resulting mixture was spread onto Sabouraud dextrose agar plate and incubated for 48 h at 37° C. The number of living strains was determined by colony count and survival percentage (%) was calculated in comparison with the number of colony (100%) obtained using 1 mM phosphate buffer as a control instead of the peptide solution.

The results are shown in FIG. 1. The antifungal effect (○) of the present peptide (JH8194Y) is compared with that of JH8194 (*) , His5:Histatin 5 (DSHEKRHHGYKRKFHEK-HHSHRGY:♦)(SEQ ID NO: 6), LFG: Bovine lactoferrin (FKCRRWQWRMKKLGAPSITCVRRAF: ■)fSEQ ID NO: 7), LFB frag (FKCRRWQWRMKKLG:▲)(SEQ ID NO: 8), and Dhvar 4: Histatin analog developed by Holland ACTA (KRLFKKLLFSLRKY: x)(SEQ ID NO: 9). The ordinate and abscissa axes of FIG. 1 indicate percentage survived of *Candida*, and the concentration of peptide, respectively. The above Histatin that is considered to have the strongest antifungal activity among a Histatin family of basic antifungal peptides existing in saliva did not show a lethal ratio of 100% in a range of 0-50 μM.

As seen from the results of FIG. 1, JH8194 showed a much stronger antifungal effect than lactoferrin and lactoferrin B, showing a lethal ratio of 100% at the concentration of 2.5 μM. However, the present peptide showed a lethal ratio of 100% at the concentration of 1.25 μM that is half that of JH8194. Considering that Minimal Fungicidal C oncentration of amphotericin B is 5 μM, it was confirmed that the present peptide had a very strong antifungal effect even a very low concentration.

Antifungal Test 2

Figure 2:
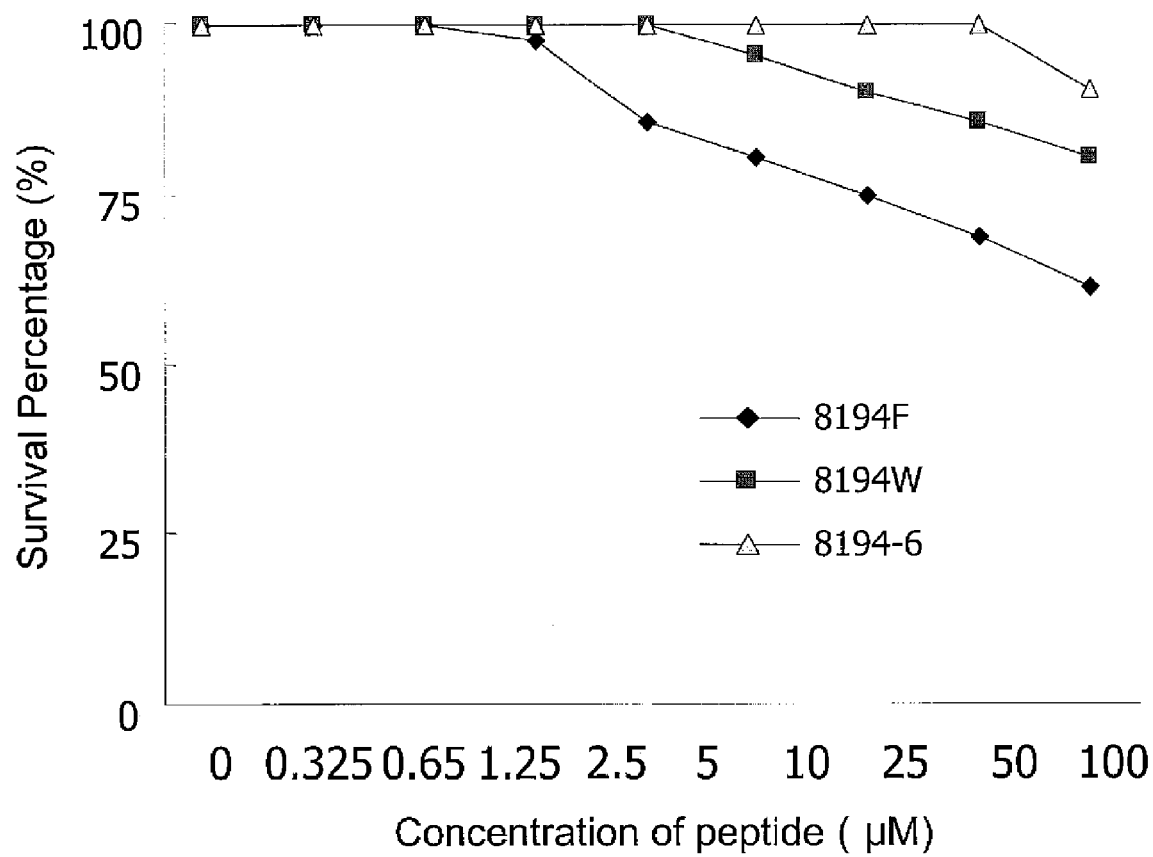
FIG. 2 is a graph showing the antifungal effects of the present peptides.

The antifungal effects of the other peptides according to the present invention were also examined in accordance with the Antifungal Test 1. The results are shown in FIG. 2.

Toxicity Test 1

Figure 3:
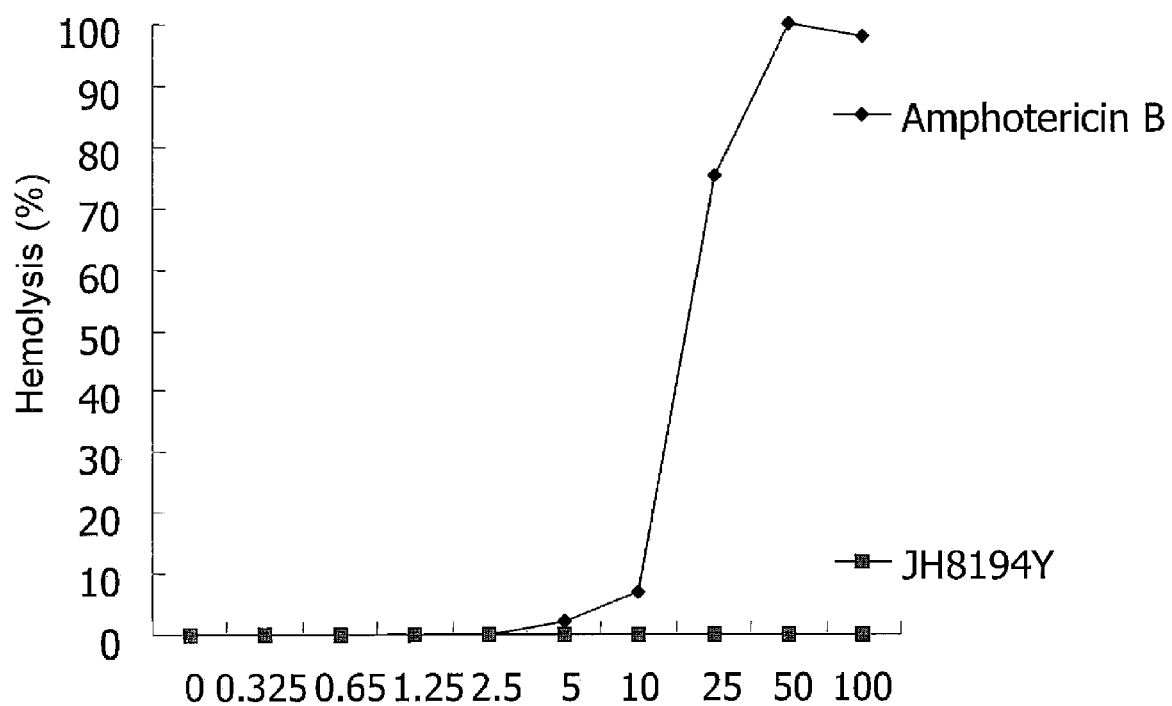
FIG. 3 is a graph showing the results obtained in a hemolytic test (toxicity test 1) of the present peptides using erythrocytes.

A final concentration of the peptides was adjusted in a range of 0.325-100 μM, and the test was done using human erythrocytes in accordance with Nikawa H, Fukushima H, Makihira S, Hamada T, Samaranayake L P. Fungicidal effect of three new synthetic cationic peptides against *Candida albicans*. Oral Dis. 2004 July; 10(4): 221-8. The results showed that the commercially available amphotericin B elicited hemolysis at 5 µM or more, while the peptide of the present invention did not exhibit hemolysis at least up to 100 µM (FIG. 3).

Toxicity Test 2

Figure 4:
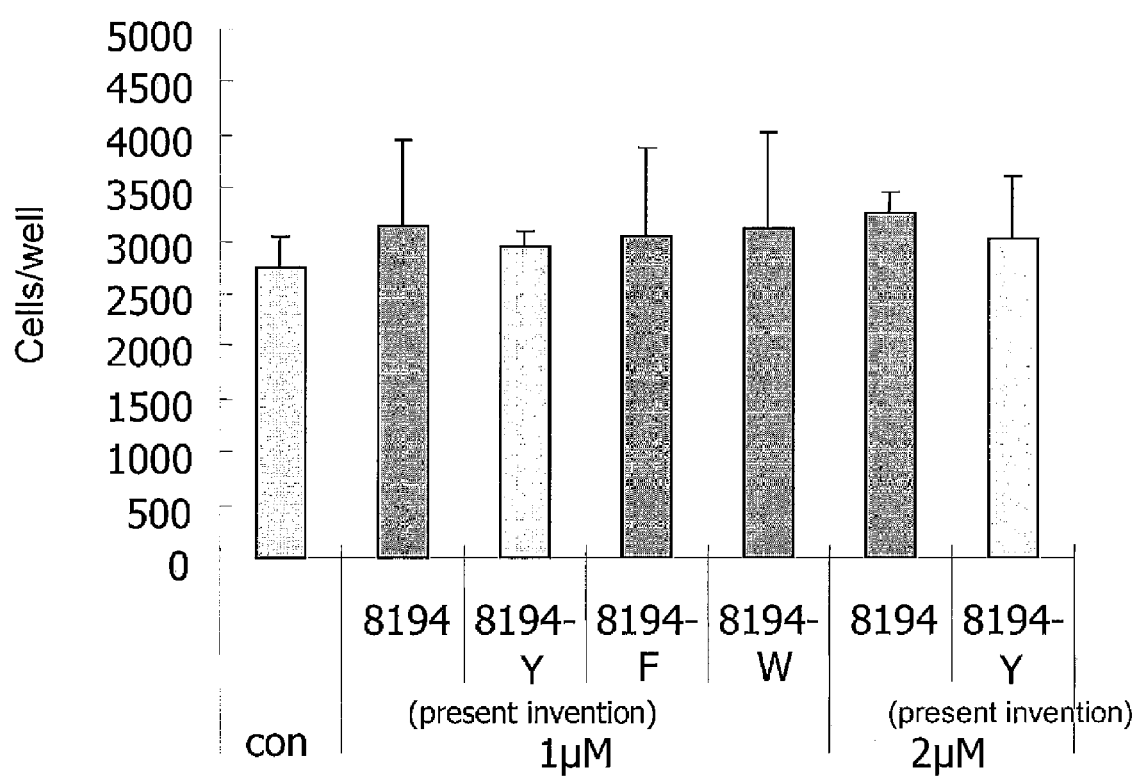
FIG. 4 is a graph showing the results obtained in a test concerning the effects of the present peptides on cell growth (toxicity test 2).

Human ilium bone-derived myelocytic mesenchymal stem cell (purchased from Cambrex Bio Science Walkersville, Inc., Walksville, Md.) (Product Code: PT-2501. Lot Numner: 4F0218) has been known to be positive for CD29, 44, 105, and 166, and negative for CD14, 34 and 45, and to have differentiating capacity into bone, cartilage and lipocyte, which will be referred to hereinafter as "MSC." The MSC was sub-cultured twice in Dulbecco's Modified Eaagle Media (Sigma Co. St. Louis, Mo.) containing an antibiotic solution (GIBOCO) comprising penicillin G at a final concentration of 100 unit/mL, Streptomycin sulfate at a final concentration of 100 µg/mL and amphotericin B at a final concentration of 0.0085%; and 10% fetal bovine serum (FBS), which will be referred to hereinafter as "Medium A", and was frozen for storage. The frozen MSC was thawed each time and cultured in Medium A to be used in the tests. Cell growth effect for human MSC was examined using basic antifungal peptides having the amino acid sequence shown as JH8194, JH8194Y, 8194F and 8194W. Human MSC was incubated in a cell growth culture medium of DMEM medium supplemented with 10% fetal calf serum and 1 µM or 2 µM of each peptide under 5% $CO_2$ at 37° C. The number of the cells was counted by means of a Coulter counter, and cytotoxicity was evaluated on the basis of a significant difference between the tested peptide and control containing no peptide. The results show that the peptirde of the present invention has no significant effect on the growth of the above human cell (FIG. 4).

INDUSTRIAL APPLICABILITY

As the peptides according to the present invention show a much remarkable antifungal and fungicidal effects than hitherto-reported antifungal peptides or antifungal agents even a very low concentration, they have great advantages in its application as an antifungal agent for medicine and research. Furthermore, as the peptides according to the present invention are a molecule with a low molecular weight consisting of 6-11 amino acids, they are industrially advantageous, for example, in synthesis with respect to its cost and the like.

What is claimed is:

1. An isolated peptide consisting of the amino acid sequence set forth in SEQ ID NO: 1.

2. A composition having a fungicidal and/or growth inhibitory function against a fungus comprising the isolated peptide according to claim 1 at a concentration of 0.3 µM to 5 µM.

3. The composition according to claim 2 wherein the fungus is *Candida, Cryptococcus,* or *Aspergillus*.

4. The composition according to claim 2 comprising the isolatedpeptide according to claim 1 at a concentration of 0.6 µM to 2.5 µM.

5. A pharmaceutical composition comprising the isolated peptide according to claim 1 at a concentration of 0.001 wt % to 0.01 wt %.

6. The pharmaceutical composition according to claim 5 further comprising at least one of lactose, glucose, mannitol, dextrin, cyclodextrin, starch, sucrose, magnesium meta-silicate aluminate, synthesized aluminum silicate, sodi um carboxylmethyl cellulose, hydroxypropyl starch, calcium carboxylmethyl cellulose, ion-exchange resin, methyl cellulose, gelatin, gum arabic, hydroxypropyl cellulose, hydroxymethyl cellulose, polyvinyl pyrrolidone, polyvinyl alcohol, soft anhydrous silicate, magnesium stearate, talc, tragacanth, bentonite, bee gum, titan oxide, sorbitan fatty acid ester, sodium laurylsulfate, glycerin. fatty acid glycerin ester, purified lanolin, glycerogelatin, polysorbate, macrogol, vegetable oil, wax, fluid paraffin, white petrolatum, fluorocarbon, nonionic surfactant, propylene glycol, and water.

7. The pharmaceutical composition according to claim 5 wherein the pharmaceutical composition is in the form of a pill, a capsule, granules, a powder, a syrup, a suspension, a suppository, an ointment, a cream, a gel agent, an adhesive skin patch, or an injectable solution.

8. A cleaning agent or collutorium comprising the isolated peptide according to claim 1 at a concentration of 0.3 µM to 5 µM.

9. The cleaning agent or collutorium according to claim 8 comprising the isolated peptide according to claim 1 at a concentration of 0.6 µM to 2.5 µM.

* * * * *

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide JH8194Y

<400> SEQUENCE: 1

Lys Arg Leu Phe Arg Arg Trp Gln Trp Arg Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide 8194F

<400> SEQUENCE: 2

Arg Arg Trp Gln Trp Arg Met Lys Lys Tyr
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide 8194W

<400> SEQUENCE: 3

Lys Arg Trp Gln Trp Arg Leu Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide 8194-6

<400> SEQUENCE: 4
```

```
Lys Arg Leu Phe Lys Tyr
1               5
```

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide JH8194

<400> SEQUENCE: 5

```
Lys Arg Leu Phe Arg Arg Trp Gln Trp Arg Met Lys Lys Tyr
1               5                   10
```

<210> SEQ ID NO 6
<211> LENGTH: 24
<212> TYPE: PRT
<213> ORGANISM: Artificial Sequence
<220> FEATURE:
<223> OTHER INFORMATION: Synthetic peptide Histatin 5

<400> SEQUENCE: 6

```
Asp Ser His Glu Lys Arg His His Gly Tyr Lys Arg Lys Phe His Glu
1               5                   10                  15

Lys His His Ser His Arg Gly Tyr
            20
```

<210> SEQ ID NO 7
<211> LENGTH: 25
<212> TYPE: PRT
<213> ORGANISM: Artificial Sequence
<220> FEATURE:
<223> OTHER INFORMATION: Synthetic peptide derived from Bovine
      lactoferrin

<400> SEQUENCE: 7

```
Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25
```

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide LFB frag

<400> SEQUENCE: 8

```
Phe Lys Cys Arg Arg Trp Gln Trp Arg Met Lys Lys Leu Gly
1               5                   10
```

<210> SEQ ID NO 9
<211> LENGTH: 14
<212> TYPE: PRT
<213> ORGANISM: Artificial Sequence
<220> FEATURE:
<223> OTHER INFORMATION: Synthetic peptide Dhvar 4

<400> SEQUENCE: 9

```
Lys Arg Leu Phe Lys Lys Leu Leu Phe Ser Leu Arg Lys Tyr
1               5                   10
```